US005217433A

United States Patent [19]

Bunin

[11] Patent Number: 5,217,433
[45] Date of Patent: Jun. 8, 1993

[54] MEDICATION CONTAINER FOR MIXING TWO COMPONENTS

[75] Inventor: Leonid Bunin, Woodbridge, N.J.

[73] Assignee: Merck & Co., Inc., Rahway, N.J.

[21] Appl. No.: 705,430

[22] Filed: May 24, 1991

[51] Int. Cl.[5] .................... A61M 37/00
[52] U.S. Cl. .................... 604/89; 604/416; 206/221; 215/DIG. 8; 222/145; 222/153
[58] Field of Search .................... 604/56, 82, 87-92, 604/244, 294, 295, 415, 416; 215/6, 247, 273-275, 280, DIG. 3, DIG. 8; 206/219, 221; 222/129, 145, 153, 420, 522, 525

[56] References Cited

U.S. PATENT DOCUMENTS

| | | | |
|---|---|---|---|
| 2,445,477 | 7/1948 | Folkman | 604/56 |
| 2,793,776 | 5/1957 | Lipari | 215/DIG. 8 |
| 2,807,384 | 9/1957 | Lipari | 215/DIG. 8 |
| 3,245,587 | 4/1966 | Brown | 222/525 |
| 3,279,654 | 10/1966 | Pierick | 604/89 |
| 3,326,416 | 6/1967 | Hayes | 222/145 |
| 3,340,873 | 9/1967 | Solowey | 128/272 |
| 3,354,883 | 11/1967 | Southerland | 128/232 |
| 3,397,694 | 7/1967 | Ogle | 128/272 |
| 3,411,503 | 11/1968 | Santomieri | 128/216 |
| 3,720,523 | 3/1973 | Nakagami | 215/6 |
| 4,330,531 | 5/1982 | Alliger | 424/149 |
| 4,331,146 | 5/1982 | Brignola | 128/218 |
| 4,412,836 | 11/1983 | Brignola | 604/87 |
| 4,822,351 | 4/1989 | Purcell | 604/411 |
| 4,865,189 | 9/1989 | Guerra et al. | 206/221 |
| 4,950,237 | 8/1990 | Henault et al. | 604/82 |

FOREIGN PATENT DOCUMENTS

| | | |
|---|---|---|
| 0069686 | 1/1983 | European Pat. Off. . |
| 0236033 | 9/1987 | European Pat. Off. . |
| 0357288 | 3/1990 | European Pat. Off. . |

*Primary Examiner*—C. Fred Rosenbaum
*Assistant Examiner*—Anthony Gutowski
*Attorney, Agent, or Firm*—Sylvia A. Ayler; Joseph F. DiPrima

[57] ABSTRACT

A bottle is provided with a dislodgeable container to hold two components of a medicament free of contact with each other until mixing is desired. One component may be a solid and the other a liquid, or both may be liquids. Mixing is accomplished by removing a locking ring and depressing the holder means.

4 Claims, 1 Drawing Sheet

MEDICATION CONTAINER FOR MIXING TWO COMPONENTS

BACKGROUND OF THE INVENTION

Dispenser devices having multiple compartments for separately enclosed materials to be mixed prior to use are disclosed in U.S. Pat. Nos. 3,340,873, 3,354,883, 3,397,694, 3,411,503, 4,331,146, 4,412,836, 4,330,531 and 4,950,237. These systems are complex, contain many parts, and are expensive to manufacture.

OBJECTS OF THE INVENTION

It is an object of the invention to provide a dispenser device having means to hold a solid and a liquid, or two liquids, separately until the time of administration. Another object is to provide a less expensive dispenser device for maintaining two components of a mixture separately until the time of administration. Still another object is to provide a more easily manufactured dispenser device for maintaining a solid and a liquid separately until the time of administration. A further object is to provide a simplified and inexpensive ophthalmic dispenser. There and other objects of the present invention will be apparent from the following description.

SUMMARY OF THE INVENTION

This invention relates to fluid dispensing devices in which solid and liquid components, or two liquid components, of a mixture are maintained in isolation from one another and in which the separated constituents can be mixed in situ, when desired, by placing the constituents in communication with one another. A container inserted in the neck of the bottle holds one compnent of the medicament e.g., a powder or a tablet, or a liquid. Locking means prevents the container from being moved. Openings in the sidewall of the container are sealed by sleeve means in the neck of the bottle when the container is locked in position in the neck. Removal of the locking means permits the container to be moved downwardly thereby exposing the openings and permitting the component in the container to mix with the component in the bottle.

Figure 1:
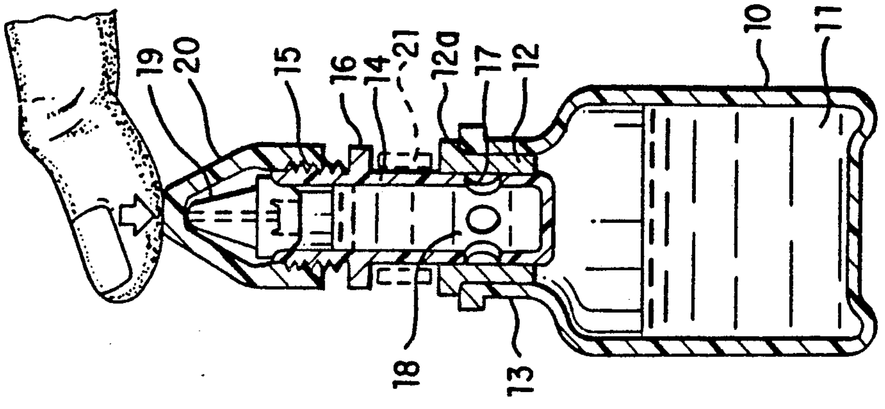
FIG. 1 is a cross-sectional side elevation of a dropper dispenser device of this invention before mixing the components.

It should be understood that the drawings are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted. It should be understood, of course, that the invention is not necessarily limited to the particular embodiments illustrated herein.

DETAILED DESCRIPTION

The dispenser device of the present invention preferably is made of a flexible plastic material, for example, low density polyethylene, and can be prepared by any suitable technique, for example, blow molding. It is to be understood that the present invention is not limited to the specific material from which the dispenser device of the present invention is made, or the particular process by which it is made as it will be understood by those skilled in the art that many different materials and various manufacturing techniques may be employed.

The dispensing device of the present invention has a dropper dispenser tip calibrated to deliver a predetermined amount of solution. Dropper dispenser tips are known in the art.

The dispensing device of the present invention comprises a bottle means 10 adapted to receive one component of a medicament, in this case liquid 11, such as, for example, a physiologically acceptable ophthalmic liquid. It is to be understood that a solid such as, for example a tablet or a powder equally may be employed but is not shown as obvious. A rubber sleeve 12 optionally having flanged end 12*a* is inserted inside the neck 13 of bottle 10. A cylindrical container 14 is partially inserted into sleeve 12. The upper end of container 14 optionally is provided with threads 15 and flange 16 to receive and to hold an overcap 20. Other types of overcaps, e.g., snap-on, equally may be used. The lower sidewall of container 14 is provided with one or more openings 17. Container 14 is filled with a liquid medicament 18 but also can be filled with a solid in the form of a powder or a tablet (not shown as obvious). If one component is a solid, the other must be a liquid. A dispenser tip 19 is inserted into the upper end of cylinder 14 and an overcap 20 is screwed onto threads 15 to protect dispenser tip 19. A locking means 21, such as a peel-off ring, is fitted around container 14 between flange 16 and flanged end 12*a* of sleeve 12 or the neck of bottle 10 if sleeve 12 lacks a flange. Locking means 21 prevents container 14 from being depressed until such time as it is desired to mix the two components.

Figure 2:
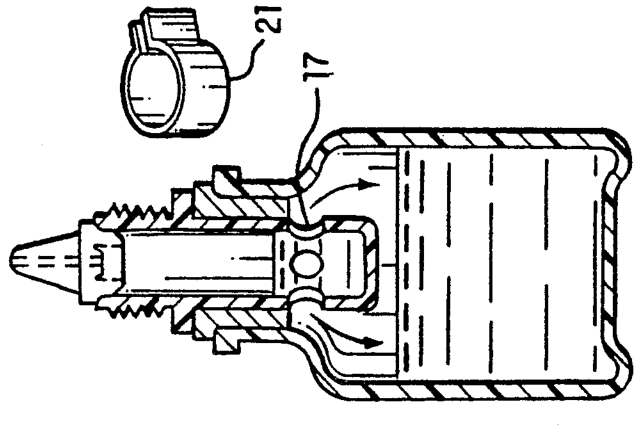
FIG. 2 is a cross-sectional side elevation of the dropper dispenser device of FIG. 1 after mixing the components.

As shown in FIG. 2, to dissolve the medicament the locking means 21 is removed and the container is lowered by pushing down on overcap 20. When the openings 17 in the lower end of container 14 move past the bottom of sleeve 12 and the bottle is tilted or inverted, the liquid and solid to contact each other.

Figure 3:
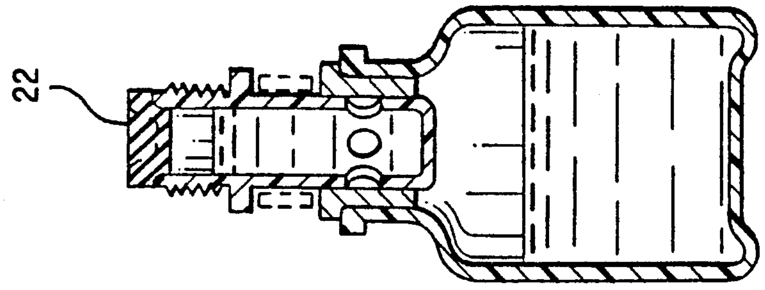
FIG. 3 is a cross-sectional side elevation of another embodiment wherein the contents are withdrawn by means of a syringe.
Figure 4:
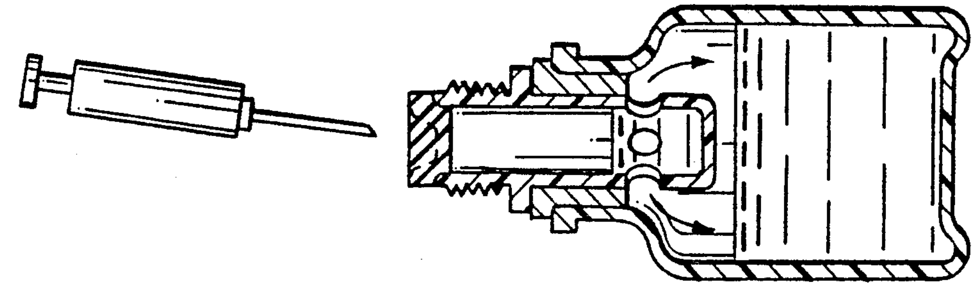
FIG. 4 is a cross-sectional side elevation of the syringe dispenser device of FIG. 3 after mixing the components.

FIGS. 3 and 4 show alternate embodiments to FIGS. 1 and 2 wherein instead of a dropper tip the upper end of container 14 is sealed with a stopper 22. After removing locking means 21 and mixing the solid and liquid contents, the stopper is pierced with the needle of a syringe and the mixed liquid is withdrawn into the syringe for administration.

What is claimed is:

1. A bottle having at its top a neck and below the neck a body adapted to hold a first component of a medicament comprising a sleeve member inserted in the neck, the sleeve member having a first flange means that does not fit into the neck of the bottle, a container means to hold a second component, the container means having openings, a lower and upper end and being disposed in the sleevemember, the upper end of the container means extending out of the bottle past the sleeve member and the part extending beyond the sleeve member being provided with a second flange means, a dislogeable locking means to hold the second component away from the first component, the locking means when in a locked position is disposed between the second flange means of the container means and the first flange means of the sleeve member such that the openings of the container means are sealed by the sleeve member and downward movement of the container means is prevented, the openings in the container means permitting the first and second components to contact one another when the locking means is dislodged, thereby deactivated, and the container means is moved downward from the neck into the body of the bottle, and an overcap attached to the upper end of the container means to close the bottle.

2. A bottle according to claim 1 wherein the upper end of the container means is provided with dispensing means.

3. A bottle according to claim 2 wherein the dispensing means is a dropper tip.

4. A bottle according to claim 2 wherein the upper end of the container means is fitted with a stopper adapted to be pierced by the needle of a syringe.

* * * * *